(12) United States Patent
Bamberg et al.

(10) Patent No.: US 9,671,372 B2
(45) Date of Patent: Jun. 6, 2017

(54) METHOD AND DEVICE FOR ASCERTAINING AN EDGE LAYER CHARACTERISTIC OF A COMPONENT

(71) Applicant: MTU Aero Engines AG, Munich (DE)

(72) Inventors: Joachim Bamberg, Dachau (DE); Roland Hessert, Herrsching (DE)

(73) Assignee: MTU AERO ENGINES AG, Munich (DE)

( * ) Notice: Subject to any disclaimer, the term of this patent is extended or adjusted under 35 U.S.C. 154(b) by 146 days.

(21) Appl. No.: 14/435,491

(22) PCT Filed: Oct. 29, 2013

(86) PCT No.: PCT/EP2013/003249
§ 371 (c)(1),
(2) Date: Apr. 14, 2015

(87) PCT Pub. No.: WO2014/067648
PCT Pub. Date: May 8, 2014

(65) Prior Publication Data
US 2015/0276683 A1    Oct. 1, 2015

(30) Foreign Application Priority Data

Oct. 31, 2012  (EP) .................................. 12 190 839

(51) Int. Cl.
*G01N 29/04* (2006.01)
*G01N 29/30* (2006.01)
*G01N 29/44* (2006.01)

(52) U.S. Cl.
CPC ........... *G01N 29/041* (2013.01); *G01N 29/30* (2013.01); *G01N 29/4409* (2013.01);
(Continued)

(58) Field of Classification Search
CPC .. G01N 29/041; G01N 29/30; G01N 29/4409; G01N 29/069; G01N 29/11;
(Continued)

(56) References Cited

U.S. PATENT DOCUMENTS 3,654,500 A * 4/1972 Claiborne .......... H03H 9/02976
257/416
4,274,288 A * 6/1981 Tittmann ............. G01N 29/041
702/166
(Continued)

FOREIGN PATENT DOCUMENTS

DE  102007009470 A1   8/2008
EP       1998175 A1  12/2008
(Continued)

*Primary Examiner* — Helen Kwok
(74) *Attorney, Agent, or Firm* — Barlow, Josephs & Holmes, Ltd.

(57) ABSTRACT

The invention relates to a method and device for ascertaining an edge layer characteristic of a component (12), in particular a component (12) for an aircraft engine. In the method, a reference body (22) with a known edge layer characteristic is arranged on the surface of the component (12). An ultrasonic wave (18) is introduced into the surfaces of the component (12) and the reference object (22) by an ultrasonic transmitter (16). An ultrasonic wave (18) resulting from the exchange between the component (12) and the reference body (22) is detected by an ultrasonic detector (20), and an edge layer characteristic of the component (12) is ascertained by an ascertaining device (28) using a difference between the generated ultrasonic wave (18) and the resulting ultrasonic wave (18).

15 Claims, 1 Drawing Sheet

(52) U.S. Cl.
CPC ............. *G01N 2291/0423* (2013.01); *G01N 2291/102* (2013.01); *G01N 2291/2694* (2013.01)

(58) Field of Classification Search
CPC ............. G01N 29/265; G01N 29/07; G01N 2291/0423; G01N 2291/102; G01N 2291/2604
See application file for complete search history.

(56) References Cited

U.S. PATENT DOCUMENTS

| | | | | | |
|---|---|---|---|---|---|
| 4,313,070 | A | * | 1/1982 | Fisher | G10K 11/36 310/313 R |
| 4,372,163 | A | * | 2/1983 | Tittmann | G01N 29/041 702/39 |
| 4,462,256 | A | * | 7/1984 | Moffett | G01N 29/041 310/313 R |
| 4,586,381 | A | * | 5/1986 | Chamuel | G01N 29/2437 73/643 |
| 4,620,443 | A | * | 11/1986 | Khuri-Yakub | G01N 29/06 73/606 |
| 5,095,465 | A | * | 3/1992 | Stokoe, II | G01N 29/041 367/14 |
| 5,113,680 | A | * | 5/1992 | Matsuura | B24C 7/00 72/53 |
| 5,894,092 | A | | 4/1999 | Lindgren et al. | |
| 7,415,880 | B2 | * | 8/2008 | Renzel | G01B 17/025 73/597 |
| 7,600,442 | B2 | * | 10/2009 | Hirose | G01N 29/069 73/579 |
| 2008/0295601 | A1 | * | 12/2008 | Chatellier | G01N 29/07 73/602 |

FOREIGN PATENT DOCUMENTS

| | | |
|---|---|---|
| JP | 9236585 A | 9/1997 |
| WO | 2006043299 A1 | 4/2006 |

* cited by examiner

METHOD AND DEVICE FOR ASCERTAINING AN EDGE LAYER CHARACTERISTIC OF A COMPONENT

BACKGROUND OF THE INVENTION

The invention relates to a method for ascertaining an edge layer characteristic of a component. In addition, the invention relates to a device for ascertaining an edge layer characteristic of a component, in particular a component for an aircraft engine.

The surfaces of highly stressed components are treated in order to increase their service life. Methods and devices for surface treatments of components are known in different configurations from prior art. Surface-treatment methods can be carried out basically by machining, lapping, eroding, coating or cleaning. For example, DE 10 2007 009 470 A1 discloses a method and a device for surface peening a component for a gas turbine of an aircraft engine. In this case, an abrasive material such as, for example, steel shot, is applied to at least one region of the surface of the component in order to obtain a surface hardening and thus an increase in the service life.

The quality of the surface treatment, i.e., the residual stress state and solidification condition of the treated component surfaces, which are introduced into the edge layer, can subsequently be determined, for example, by X-ray diffraction with electrochemical erosion or by the so-called borehole method, in order to establish a service life prognosis. However, in this case, destructive test methods are involved. In addition, an indirect monitoring by means of reference samples (Almen plates) that are hardened with the component can be carried out on individual, well-accessible component regions. However, this makes possible only very limited information on the quality of the entire solidified region of the component. Alternatively, it is known to evaluate the quality of the surface treatment by synchrotron radiation or by neutron scattering. These types of measurement methods, however, require an enormous apparatus expenditure as well as the use of radioactive radiation sources and also only make possible the measuring of the simplest component geometries with low spatial resolution.

BRIEF SUMMARY OF THE INVENTION

The object of the present invention is to make possible a simpler, more flexible and non-destructive determination of the edge layer characteristic of a component.

The object is achieved according to method and device of the present invention. Advantageous embodiments with appropriate enhancements of the invention are indicated in the claims, wherein advantageous embodiments of the method are to be viewed as advantageous embodiments of the device, and vice versa.

In the method according to the invention, in order to ascertain an edge layer characteristic of a component, in particular a component for an aircraft engine, a reference object with a known edge layer characteristic is disposed on the surface of the component. At least one ultrasonic wave is introduced into the surfaces of the component and the reference object by means of an ultrasonic transmitter. Subsequently, at least one ultrasonic wave resulting from the interaction between the component and the reference object is detected by means of an ultrasonic detector, and an edge layer characteristic of the component is ascertained via an ascertaining device, based on a difference between the at least one ultrasonic wave that is generated and the at least one ultrasonic wave that results. Unlike the method known from the prior art for ascertaining the edge layer characteristic of components, the method according to the invention makes possible a particularly simple, flexible, and above all, non-destructive determination of the edge layer characteristic. By generating an ultrasonic surface wave, which is also called a Rayleigh wave, by means of the ultrasonic transmitter, in the edge layer of the component and in the surface of the reference object, there are characteristic interactions of the ultrasonic wave with the materials of the component and of the reference object. Based on the known edge layer characteristic of the reference object, a direct comparative analysis of the resulting sound velocity of the at least one ultrasonic wave via the ultrasonic detector can result. The sound velocity of the ultrasonic wave in this case essentially depends on the elastic properties of the component material and of the reference object. The reference object or the reference objects in this case can be produced with exactly defined edge layer characteristics and solidification conditions. Changes in the edge layer properties and surface properties of the component thus lead to corresponding changes in the sound velocity and to changes in the interaction with the reference object and can be evaluated with the aid of the ascertaining device, whereby information can be obtained on the quality and nature of the edge layer of the component. In other words, the ascertaining of the edge layer characteristic is based on a comparative measurement. Unlike the prior art, the method according to the invention permits a non-destructive and comparative measurement and a monitoring of the quality and edge layer characteristic of the component. The method according to the invention is moreover suitable for characterizing any edge layer systems or surfaces, for example, for characterizing hardened surfaces or coatings. In addition, components with difficultly accessible surface regions and complex geometries, for example with curved surfaces, can also be monitored without problem. The method according to the invention can also be carried out very rapidly. Thus, an official authorization of this measurement technique or this method is also possible, for example, for the evaluation and service life prognosis of components for aircraft engines that can be highly stressed. Basically, it can also be provided that the reference object is removed at times from the component, so that any difference between the generated ultrasonic wave and a resulting ultrasonic wave can also be additionally considered without the applied reference object, for ascertaining the edge layer characteristic. In this way, a further improvement of the ascertained result for the edge layer characteristic of the component can be achieved.

In an advantageous embodiment of the invention, it is provided that the edge layer characteristic of the component is ascertained before and/or after a surface treatment of the component. The edge layer characteristic of the component can be determined prior to the surface treatment in order to be better able to estimate the extent and the details of the required surface or edge layer treatment. In addition, it may be provided that the edge layer characteristic of the component is ascertained after the surface treatment, whereby the completeness and the success of the surface or edge layer treatment can advantageously be examined.

Further advantages result due to the fact that at least one method parameter of the surface treatment is controlled and/or regulated as a function of the ascertained edge layer characteristic. In this way, a particularly high component quality is achieved, since the method parameters can be optimally adjusted as a function of the individual state of the treated component in each case. For example, the transmitted energy in shot peening essentially depends on mass, impact velocity, impact angle and hardness of the shot grains, on the number of shot hits, and the surface nature of the shot material. The surface treatment can thus be influenced in a targeted manner via method parameters such as the material and geometry of the shot material, particle speed, traversing speed of the surface treatment means over the surface, and the like. In this way, the surface treatment of the component not only can be carried out particularly quickly, but also in a particularly reproducible manner and quantitatively, whereby particularly high savings in operating time and cost can be realized.

Further advantages result if at least one ultrasonic wave with a frequency between 5 MHz and 10 MHz is generated by means of the ultrasonic transmitter. Below a frequency between 5 MHz and 10 MHZ are to be understood, in particular, frequencies of 5.0 MHz, 5.5 MHz, 6.0 MHz, 6.5 MHz, 7.0 MHz, 7.5MHz, 8.0 MHz, 8.5 MHz, 9.0 MHz, 9.5 MHz or 10.0 MHz, as well as corresponding intermediate frequencies. Components of the most varied materials, for example, materials based on titanium or nickel, can be optimally monitored thereby, since the frequency of the ultrasonic wave can be optimally adapted to the elastic properties of the respective material.

In another advantageous embodiment of the invention, it is provided that a dispersion analysis method is used for ascertaining the edge layer characteristic, and/or that a depth profile of the component is ascertained by means of the ascertaining device. If an ultrasonic wave is non-dispersive, its sound velocity is independent of its frequency. In other words, the velocity of a Rayleigh wave does not change when its frequency is changed. Since hardened components, in particular, components for aircraft engines, however, possess a dispersive edge layer, the sound velocity of the Rayleigh wave, which is generated at the surface of the component, is dependent on its frequency. The spatial and temporal distribution of the sound velocity changes thereby. A particularly exact, spatially resolved edge layer characteristic of the component can therefore be ascertained advantageously by means of a dispersion analysis. If the wavelength of an ultrasonic wave is increased, the penetration depth of the Rayleigh wave into the component also increases. In first approximation, the penetration depth of a Rayleigh wave essentially corresponds to its wavelength, but varies as a function of the material properties of the component. A depth profile of the component can be ascertained advantageously thereby with the help of the method according to the invention, whereby particularly precise information on the quality of the surface treatment is possible.

In another advantageous embodiment of the invention, it is provided that several ultrasonic waves of the same frequency and/or several ultrasonic waves of different frequencies and/or at least one broadband ultrasonic wave is or are generated by means of the ultrasonic transmitter. This represents another possibility for being able to obtain particularly precise information on the quality and nature of the surface or of the edge layer of the component, as a function of the material and the geometry of the component, as well as the surface treatment method which is used. Alternatively or additionally, it has also been shown to be of advantage if ultrasonic waves pulsed by means of the ultrasonic transmitter are generated particularly with a pulse frequency between 500 $s^{-1}$ and 1500 $s^{-1}$. It is possible in this way to ascertain the nature of the edge layer of the component based on sound reflection. For example, several short ultrasonic pulses per second can be beamed into the surface of the component and the velocity of the reflected ultrasonic waves can be determined over time windows.

Further advantages result when a hardening method is conducted as a surface treatment. In this way, a considerable prolongation of service life can be achieved, in particular, for a highly stressed component, such as a component for an aircraft engine, for example. The ascertaining of the edge layer characteristic by means of Rayleigh waves advantageously does not adversely affect the hardening method.

Thus, it has been shown to be advantageous when shot peening and/or ultrasonic shot peening and/or hard rolling and/or laser shock peening is used as the hardening method. In this way, the advantages that can be obtained by the method according to the invention for different components and different types of surface treatment can be realized.

By using a component made of a polycrystalline and/or monocrystalline and/or high-temperature-resistant material, a particularly long service life of the component is also assured under later extreme operating conditions, such as prevail, for example, in aircraft engines. Alternatively or additionally, work time or labor time and cost advantages especially can be achieved, if a compressor disk and/or a turbine disk and/or a blade/vane and/or a shaft of a gas turbine, particularly of an aircraft engine, is used as the component. If the at least one reference object and the component are made of the same material and preferably also possess the same material structure or the same hardened edge layer state, at least in regions, the ultrasonic wave introduced into the component and the reference object is changed to the smallest extent, so that the difference between the generated and the detected ultrasonic wave is minimized. By applying a reference object, which is composed of the same material as the component and already has the desired surface condition for the component, for example, the desired edge layer hardening, the edge layer characteristic, for example, the solidification condition, of the component can thus be verified in a particularly simple and reliable manner.

In another advantageous embodiment of the invention, it is provided that an acoustic coupling means, in particular water and/or a gel, is disposed at least between the component and the reference object. The coupling means in this case produces a contact between the component and the reference object that is as optimal as possible, whereby a corresponding improvement in the ascertaining result is achieved. The coupling means in this case should be free of air bubbles or should be degassed in order to permanently assure sound transmission that is as free of gaps as possible. Basically, it can be provided here that the same or a different coupling means is also disposed between the ultrasonic transmitter and/or the ultrasonic detector and the component and/or the reference object, in order to assure an improved sound transmission.

In another advantageous embodiment of the invention, it is provided that the edge layer characteristic of the reference object is ascertained by x-ray diffraction analysis with stepwise chemical erosion, and/or by borehole analysis and or by synchrotron radiation analysis, and/or by neutron scattering analysis, prior to arranging it on the component. In other words, it is provided that the edge layer characteristic of the reference object is ascertained first with familiar techniques and test methods known from the prior art. Since the reference object, unlike the component, may have simple geometry, another possibility for improving the result ascertained for the edge layer characteristic of the component is given thereby.

In this case, in a further embodiment of the invention, the method can be carried out in a particularly flexible manner if the ultrasonic transmitter and/or the ultrasonic detector is/are disposed on the component and/or on the reference object. For example, by disposing the ultrasonic detector on the reference object, the entire surface of the component can be examined rapidly over a large area by moving the reference object correspondingly over the component. In this case, the ultrasonic transmitter can be arranged in a fixed or movable position on the component or also on the reference object. Likewise, the ultrasonic detector can be disposed in a fixed or movable position on the component, whereas the ultrasonic transmitter is disposed on the reference object.

Another aspect of the invention relates to a device for ascertaining an edge layer characteristic of a component, in particular a component for an aircraft engine, wherein a simpler, more flexible and non-destructive ascertaining of the edge layer characteristic of a component according to the invention is made possible, in that the device comprises a reference object with a known edge layer characteristic, which can be disposed on the surface of the component. In addition, the device comprises an ultrasonic transmitter, by means of which at least one ultrasonic wave can be introduced into the surfaces of the component and of the reference object disposed on the component, as well as an ultrasonic detector, by means of which at least one ultrasonic wave resulting from the interaction between the component and the reference object can be detected. In order to ascertain the edge layer characteristic of the component, based on a difference between the at least one generated ultrasonic wave and the at least one resulting ultrasonic wave, in addition, the device comprises an ascertaining device formed correspondingly. Unlike the devices known from the prior art for ascertaining the edge layer characteristic of components, the device according to the invention makes possible a particularly simple, flexible, and above all non-destructive ascertaining of the edge layer characteristic. By being able to generate an ultrasonic surface wave, which is also called a Rayleigh wave, in the surface of the component and in the surface of the reference object by means of the ultrasonic transmitter, characteristic interactions of the ultrasonic wave with the materials of the component and of the reference object can be generated. Based on the known edge layer characteristic of the reference object, a direct comparative analysis of the resulting sound velocity of the at least one ultrasonic wave can result via the ultrasonic detector. The sound velocity of the ultrasonic wave in this case essentially depends on the elastic properties of the component material and the reference object. The reference object or the reference objects in this case can be produced with exactly defined edge layer characteristics and hardening states. Changes in the surface properties of the component thus lead to corresponding changes in the sound velocity and to changes in the interaction with the reference object and can be evaluated with the aid of the ascertaining device, whereby information can be obtained on the quality and nature of the edge layer of the component. In other words, the ascertaining of the edge layer characteristic is based on a comparative measurement. The device according to the invention is moreover suitable for characterizing any edge layer system or surface, for example, for characterizing hardened surfaces or coatings. In addition, components with difficultly accessible surface regions and complex geometries, for example with curved surfaces, can also be monitored without problem. The device according to the invention also permits a very rapid ascertaining of the edge layer characteristic. Thus, an official authorization of this measuring system or this device is possible, for example, for the evaluation and service life prognosis of components for aircraft engines that can be highly stressed. Preferably, the device according to the invention is designed for conducting a method according to one of the preceding embodiment examples. The advantages resulting therefrom can be derived from the preceding descriptions of the method according to the invention.

Thus, it has been shown to be advantageous if the ascertaining device is coupled for data exchange to the ultrasonic transmitter and/or to the ultrasonic detector. In this case, the ascertaining device can draw on the wave properties of the generated and/or detected ultrasonic wave(s) in a particularly simple manner and for evaluating the surface nature of the component in the processed region.

Further advantages result by coupling the ascertaining device for data exchange to a control and/or regulating system of a surface treatment means, wherein the control and/or regulating system is preferably designed to control and/or to regulate at least one method parameter of the surface treatment means as a function of the ascertained edge layer characteristic. This makes possible a direct intervention in a surface treatment of the component, depending on the ascertained edge layer characteristic, whereby the surface treatment of the component can be conducted particularly rapidly, precisely and reproducibly. In addition, this control/regulating system can reliably prevent the component from being surface-treated in a faulty manner, whereby possibly irreparable damage of the component is prevented or potential post-treatment steps are reliably avoided.

BRIEF DESCRIPTION OF THE DRAWINGS

Further features of the invention result from the claims, the embodiment examples as well as on the basis of the drawings. The features and combinations of features named in the preceding description, as well as the features and combinations of features named in the examples of embodiment below can be used not only in the combination indicated in each case, but also in other combinations, without departing from the scope of the invention. Herein:

DETAILED DESCRIPTION OF THE INVENTION

Figure 1:
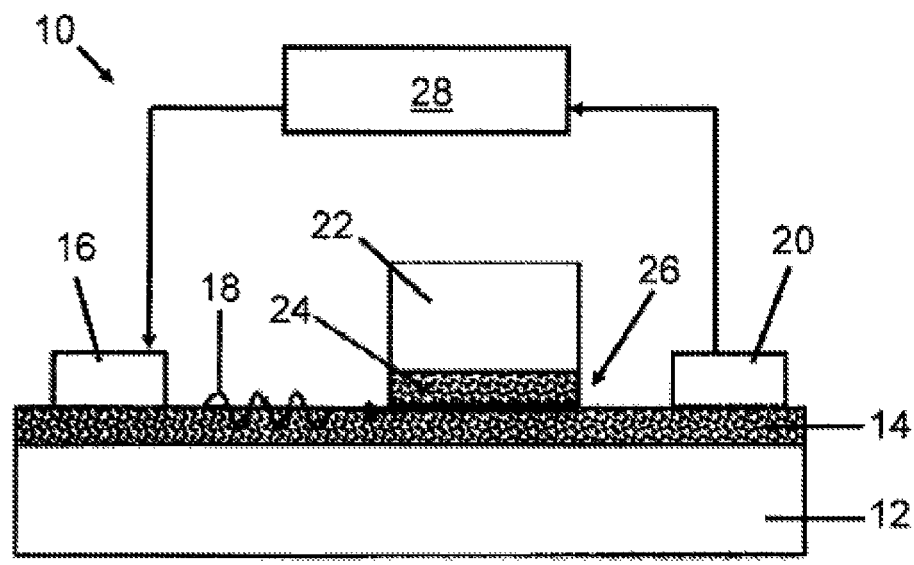
FIG. 1 shows a schematic lateral sectional view of a device according to the invention for ascertaining an edge layer characteristic of a component.

FIG. 1 shows a schematic lateral sectional view of a device 10 according to the invention for ascertaining an edge layer characteristic of a component 12, which is designed presently as a compressor disk for an aircraft engine and is composed of a high-temperature-resistant material, such as Inconel 718 or Titan 64. Shot material was applied to the component 12 in a way known in and of itself by means of a surface treatment means (not shown) designed as a shot peening apparatus, in order to achieve a hardened region 14 in the edge region of the surface. The edge layer hardening of the component 12 takes place, for example, with a peening intensity corresponding to 0.1-0.25 mm A Almen and with a depth between 100 µm and 300 µm.

For the monitoring of the surface treatment method and the edge layer characteristic of the component 12, the device 10 comprises an ultrasonic transmitter 16, by means of which ultrasonic waves 18 with frequencies between 5 MHz and 10 MHz, at least in the region 14 to be hardened on the surface of the component 12, are generated before and/or after the surface treatment. The ultrasonic waves 18 can be generated continuously or as sound pulses, for example, at 1000 pulses per second. The ultrasonic transmitter 16 is disposed directly on the surface of the component 12 in the example of embodiment shown. The ultrasonic waves 18, which are also called Rayleigh waves, travel as surface waves to an ultrasonic detector 20 of device 10, which is distanced from the ultrasonic transmitter 16, the ultrasonic waves 18 resulting from the interaction with the component 12 being detected by means of this detector 20.

A reference object 22 is disposed between the ultrasonic transmitter 16 and the ultrasonic detector 20 in the sound path of the ultrasonic wave 18 on the surface of the component 12. The reference object 22 is composed of the same material as the component 12 and possesses a known surface characteristic or edge layer characteristic. For this purpose, the reference object 22 in its turn has a hardened region 24, whose material structure corresponds to that of the region 14 of the component 12 to be treated. Alternatively, it can be provided that the reference object 22 is composed entirely of the defined material structure. For better sound transmission, an acoustic coupling means 26, which can be water or a gel, for example, is disposed between the component 12 and the reference object 22.

In addition, the device 10 comprises an ascertaining device 28, which is coupled to the ultrasonic transmitter 16 and the ultrasonic detector 20 for data exchange, and by means of this ascertaining device, an edge layer characteristic of the component 12 is ascertained in the treated region 14, based on a difference between the generated ultrasonic wave(s) 18 and the detected ultrasonic wave(s) 18, so that a comparative analysis of the surface hardening is given. By varying the frequency, regions of different depth can be detected. The ascertaining device 28 can ascertain the edge layer characteristic, for example, by dispersion analysis. By varying the frequencies of the ultrasonic waves 18, it is also possible to create a depth profile of the component 12. In addition, it can be provided that the ascertaining device 28 is coupled for data exchange to a control and/or regulating system (not shown) of the surface treatment means, in order to control and/or to regulate method parameters of the surface treatment means as a function of the ascertained edge layer characteristic of the component 12.

By applying the reference object 22 onto the surface of the component 12 to be examined, the generated ultrasonic wave 18 interacts with both the surface of the component 12, as well as also with the surface of the reference object 22. If the reference object 22 and the component 12 are composed of the same material, have the same material structure and the same hardened edge layer state, the ultrasonic wave 18 varies to the smallest extent. By applying the reference object 22 with the desired edge layer hardening (region 24), the solidification condition of the component 12 can be examined and verified. The reference object 22 in this case can basically be moved one or more times onto the surface of the component 12. In addition, it can be provided that several, if need be, differently designed reference objects 22 can be used and the resulting interferences of the ultrasonic waves 18 can be drawn on for ascertaining the edge layer characteristic. Additionally, different reference objects 22 can be disposed one behind the other on the component 12, and the ultrasonic waves 18 resulting in each case can be detected and drawn on for ascertaining the edge layer characteristic.

Figure 2:
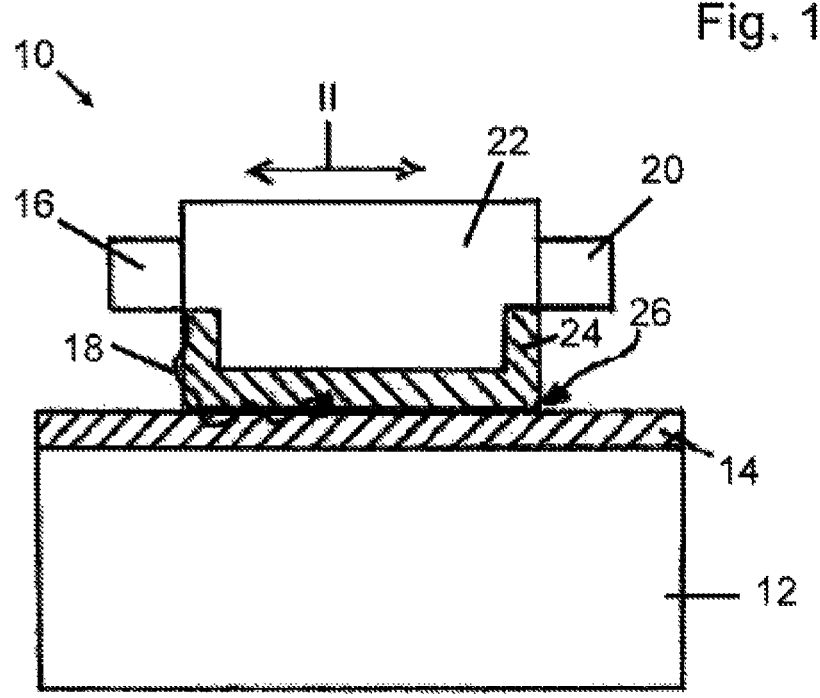
FIG. 2 shows a schematic lateral sectional view of an alternative embodiment of the device.

FIG. 2 shows a schematic, lateral sectional view of an alternative embodiment of the device 10. Unlike the preceding example of embodiment, in this case, both the ultrasonic transmitter 16 as well as the ultrasonic detector 20 are attached to the reference object 22. The ascertaining device 28 is not shown for reasons of clarity. The ultrasonic waves 18 are introduced first into the reference object 22 and propagate "around the corner" via the coupling means 26 into the hardened region 14 of the component 12. From there, the ultrasonic waves 18 travel along the bearing surface of the reference object 22 up to the edge of the reference object 22 and from there to the ultrasonic detector 20, which detects the ultrasonic waves 18 resulting from the interaction. Thus, the ultrasonic waves 18 in this configuration of the device 10 interact with both the component 12 or with its hardened region 14, as well as with the reference object 22 or with its hardened region 24, whereby the edge layer characteristic of the component 12 can be determined. Since both the ultrasonic transmitter 16 as well as the ultrasonic detector 20 are attached to the reference object 22, they can be moved jointly with it over the surface of the component 12, according to double arrow II. Components 12 with large areas may also be "scanned" rapidly and precisely thereby, so that basically the edge layer characteristic of the entire surface of the component 12 can be ascertained.

The parameter values indicated in the documents for defining process and measurement conditions for the characterization of specific properties of the subject of the invention are also to be viewed as within the framework of deviations—for example, based on measurement errors, system errors, weighing errors, DIN tolerances and the like—and are encompassed by the scope of the invention.

The invention claimed is:

1. A method for ascertaining an edge layer characteristic of a component (12) for an aircraft engine, comprising the steps of:
    disposing a reference object (22) with a known edge layer characteristic on a surface of the component (12);
    introducing at least one ultrasonic wave (18) into the surfaces of the component (12) and the reference object (22) by an ultrasonic transmitter (16);
    detecting at least one ultrasonic wave (18) resulting from an interaction with the component (12) and the reference object (22) by an ultrasonic detector (20); and
    ascertaining an edge layer characteristic of the component (12) by an ascertaining device (28), based on a difference between the at least one ultrasonic wave (18) that is introduced and the at least one ultrasonic wave (18) that is detected and interference of the at least one ultrasonic wave with the reference object (22).

2. The method according to claim 1, wherein the edge layer characteristic of the component (12) is ascertained before and/or after a surface treatment of the component (12).

3. The method according to claim 2, wherein at least one method parameter of the surface treatment is controlled and/or regulated as a function of the ascertained edge layer characteristic.

4. The method according to claim 1, wherein the at least one ultrasonic wave (18) with a frequency between 5 MHz and 10 MHz is generated by the ultrasonic transmitter (16).

5. The method according to claim 1, wherein a dispersion analysis method is used for ascertaining the edge layer characteristic and/or that a depth profile of the component (12) is ascertained by the ascertaining device (28).

6. The method according to claim 1, wherein several ultrasonic waves (18) of the same frequency and/or several ultrasonic waves (18) of different frequencies and/or at least one broadband ultrasonic wave (18) and/or pulsed ultrasonic waves (18) with a pulse frequency between 500 $s^{-1}$ and 1500 $s^{-1}$ is or are generated.

7. The method according to claim 2, wherein a hardening method is conducted as a surface treatment.

8. The method according to claim 7, wherein shot peening and/or ultrasonic shot peening and/or hard rolling and/or laser shock peening is used as the hardening method.

9. The method according to claim 1, wherein the component (12) made of a polycrystalline and/or monocrystalline and/or high-temperature-resistant material is used, and/or that a compressor disk and/or a turbine disk and/or a blade/vane and/or a shaft of a gas turbine of an aircraft engine, is used as the component (12), and/or that the component (12) and the reference object (22) are composed of the same material and same material structure, at least in regions thereof.

10. The method according to claim 1, further comprising the step of:

disposing a layer of water and/or a gel (26) at least between the component (12) and the reference object (22), the layer of water and/or gel (26) configured to propagate the at least one ultrasonic wave (18) from the ultrasonic transmitter (16) into the surfaces of the component (12) and the reference object (22).

11. The method according to claim 1, wherein the edge layer characteristic of the reference object (22) is ascertained by x-ray diffraction analysis with stepwise chemical erosion, and/or by borehole analysis and/or by synchrotron radiation analysis, and/or by neutron scattering analysis, prior to arranging on the component (12).

12. The method according to claim 1, wherein the ultrasonic transmitter (16) and/or the ultrasonic detector (20) is or are disposed on the component (12) and/or on the reference object (22).

13. A device (10) for ascertaining an edge layer characteristic of a component (12) for an aircraft engine, comprising:

a reference object (22) with a known edge layer characteristic, which can be disposed on a surface of the component (12);

an ultrasonic transmitter (16), by which at least one ultrasonic wave (18) can be introduced into the surfaces of the component (12) and of the reference object (22) disposed on the component (12);

an ultrasonic detector (20), by which at least one ultrasonic wave (18) resulting from an interaction between the component (12) and the reference object (22) can be detected; and an ascertaining device (28), by which an edge layer characteristic of the component (12) can be ascertained, based on a difference between the at least one ultrasonic wave (18) that is introduced and the at least one ultrasonic wave (18) that is detected.

14. The device (10) according to claim 13, wherein the ascertaining device (28) is coupled for data exchange to the ultrasonic transmitter (16) and/or to the ultrasonic detector (20).

15. The device (10) according to claim 13, wherein the ascertaining device (28) is coupled for data exchange to a control and/or the regulating system of a surface treatment means for the surface treatment of the component (12), wherein the control and/or regulating system is designed to control and/or to regulate at least one method parameter of the surface treatment means as a function of the ascertained edge layer characteristic.

* * * * *